(12) United States Patent
Tanio et al.

(10) Patent No.: US 7,744,578 B2
(45) Date of Patent: Jun. 29, 2010

(54) ABSORBENT ARTICLE

(75) Inventors: Toshiyuki Tanio, Kagawa (JP);
Masataka Kinoshita, Kagawa (JP);
Kazuya Nishitani, Kagawa (JP);
Noritatsu Tamagawa, Kagawa (JP)

(73) Assignee: Uni-Charm Corporation, Ehime-Ken (JP)

( * ) Notice: Subject to any disclaimer, the term of this patent is extended or adjusted under 35 U.S.C. 154(b) by 16 days.

(21) Appl. No.: 10/847,823

(22) Filed: May 17, 2004

(65) Prior Publication Data

US 2004/0249355 A1 Dec. 9, 2004

(30) Foreign Application Priority Data

Jun. 9, 2003 (JP) .............................. 2003-163134

(51) Int. Cl.
*A61F 13/15* (2006.01)
*A61F 13/20* (2006.01)

(52) U.S. Cl. .............................. 604/385.27; 604/385.24

(58) Field of Classification Search ......... 604/379–380, 604/385.12, 385.24–385.28
See application file for complete search history.

(56) References Cited

U.S. PATENT DOCUMENTS

| 4,014,338 | A | * | 3/1977 | Schaar ........................ 604/389 |
| 5,221,275 | A | * | 6/1993 | Van Iten ...................... 604/387 |
| 5,582,606 | A | | 12/1996 | Bruemmer et al. |
| 6,248,098 | B1 | * | 6/2001 | Sayama ................. 604/385.28 |
| 6,508,796 | B2 | | 1/2003 | Mizutani et al. |
| 6,569,140 | B1 | | 5/2003 | Mizutani et al. |
| 7,335,810 | B2 | | 2/2008 | Yoshimasa et al. |
| 2001/0056268 | A1 | * | 12/2001 | Mizutani et al. ............ 604/365 |
| 2003/0028167 | A1 | * | 2/2003 | Kashiwagi et al. ..... 604/385.04 |
| 2003/0088222 | A1 | | 5/2003 | Yoshimasa et al. |
| 2003/0093056 | A1 | * | 5/2003 | Kurata ................. 604/385.101 |
| 2003/0144644 | A1 | * | 7/2003 | Murai et al. ........... 604/385.27 |

FOREIGN PATENT DOCUMENTS

| JP | 64-068503 A1 | 3/1989 |
| JP | 04-012751 A1 | 1/1992 |
| JP | 2000-288012 | 10/2000 |
| JP | 2000-316905 | 11/2000 |
| JP | 2001-095842 A1 | 4/2001 |
| JP | 200195844 | 4/2001 |
| JP | 2002-000656 A1 | 1/2002 |
| JP | 2002-291806 | 10/2002 |
| JP | 2003-024372 | 1/2003 |
| JP | 2003-245306 | 9/2003 |

OTHER PUBLICATIONS

JP 2004-154154 to Tamura et al, English abstract.*

(Continued)

*Primary Examiner*—Melanie J Hand
(74) *Attorney, Agent, or Firm*—Morrison & Foerster LLP

(57) ABSTRACT

An absorbent article having leakage preventing walls that longitudinally exert an elastic contractive force to bend a main body. Each leakage preventing wall is provided, between front and rear ends, with a constraint portion so as to locally constrain an allowable rising height of the leakage preventing wall. Thus, the leakage preventing wall takes a shape that can easily conform to a curved surface of the wearer's body.

18 Claims, 9 Drawing Sheets

OTHER PUBLICATIONS

English translation of JP 2000-316905 A.*

Tamagawa et al., "Sanitary Napkin", U.S. Appl. No. 10/862,928, filed Jun. 7, 2004.

Nishitani et al., "Sanitary Napkin", U.S. Appl. No. 10/862,926, filed Jun. 7, 2004.

Kinoshita et al., "Sanitary Napkin", U.S. Appl. No. 10/841,363, filed May 7, 2004.

* cited by examiner

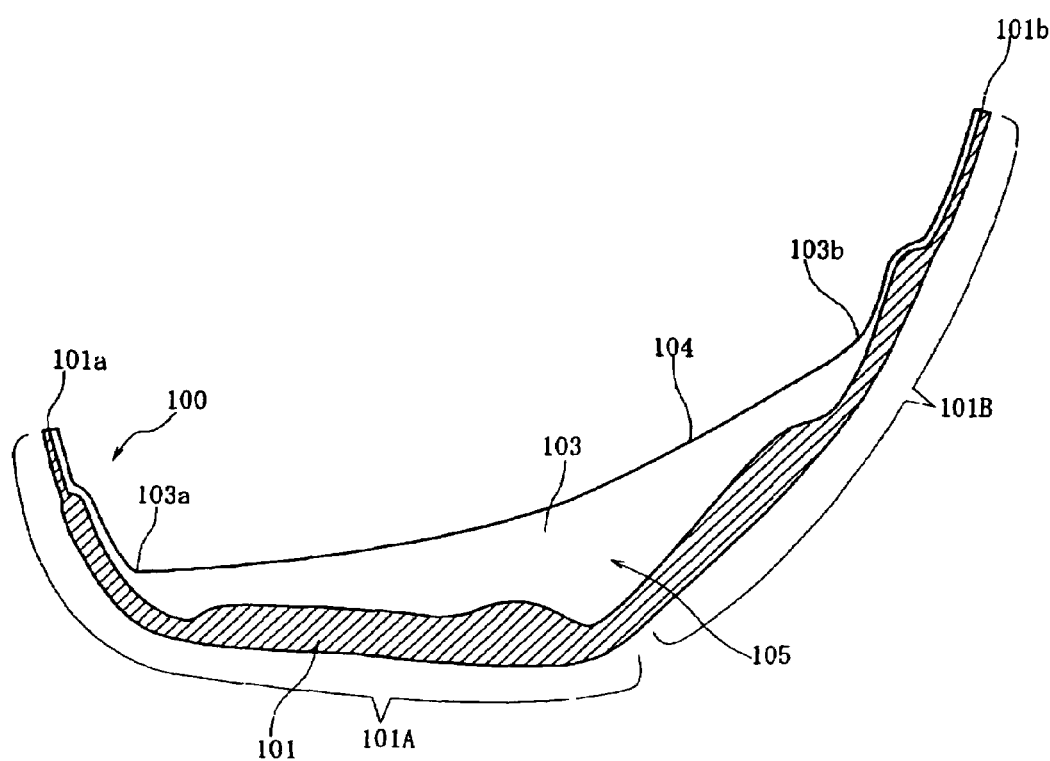

ABSORBENT ARTICLE

BACKGROUND OF THE INVENTION

1. Field of the Invention

The present invention relates to an absorbent article such as elongated sanitary napkin suitable for nighttime use, disposable diaper, or urine absorbing pad to be worn inside an undergarment, diaper, etc. More particularly, the invention relates to an absorbent article with longitudinally extending leakage preventing walls disposed on right and left side portions of the skin-side surface.

2. Description of the Related Art

Sanitary napkins disclosed in Japanese Unexamined Patent Publication No. 2001-95842 (Patent Publication 1) and Japanese Unexamined Patent Publication No. 2002-656 (Patent Publication 2) are so elongated as to be suitable for nighttime use. This type of sanitary napkin is designed to be worn such that its front portion faces the vaginal opening being a menstrual blood excretory part while its intermediate and rear portions contact the perineum and the anus so that the rear portion faces the cleft of the buttocks. On the ski-side surface of the sanitary napkin, leakage preventing walls are provided to extend from the front portion to the rear portion on both right and left side portions of the sanitary napkin. These leakage preventing walls are allowed to rise from the skin-side surface over a long distance from adjacent a portion intended to face the vaginal opening to a portion intended to face the buttocks. With the leakage prevented walls present in a space between the skin-side surface of the sanitary napkin and the wearer's body, body liquid such as menstrual blood trying to flow down the perineum and the anus toward the posterior region during sleep may be blocked by the leakage preventing walls.

Japanese Unexamined Patent Publication No. S64-68503 (Patent Publication 3) discloses a disposable diaper, and Japanese Unexamined Patent Publication No. H04-12751 (Patent Publication 4) discloses a urine absorbing pad to be worn along with a diaper cover, undergarment or the like for absorption of urine.

Also in the disposable diaper and the urine absorbing pad, longitudinally extending leakage preventing walls are disposed on the skin-side surface at right and left side portions thereof. The disposable diaper and the urine absorbing pad are designed to be worn from the crotch to the buttocks, wherein the leakage preventing walls are allowed to rise toward the wearer's body from the crotch to the buttocks, coming into close contact with the wearer's body.

These absorbent articles disclosed in Patent Publications 1 to 4 are all elongated so as to be worn from the crotch to the buttocks. FIG. 14 is a sectional view of a conventional elongated absorbent article 100, diagrammatically showing how leakage preventing walls rise in a deformed article.

The absorbent article 100 has a main body 101 composed of a liquid-permeable topsheet, a liquid absorbent layer, and a liquid-impermeable backsheet. The main body 101 is intended to be worn such that its front end edge 101a is directed toward the lower abdomen while its rear end edge 101b is directed toward the buttocks. Leakage preventing walls 103 are fixed to the main body 101 at their front and rear ends 103a, 103b. The leakage preventing walls 103 exert an elastic contractive force to bring the front and rear ends 103a, 103b closer to each other, whereby the main body 101 is deformed with its skin-side surface being concavely curved. As a result, the leakage preventing walls 103 rise with their longitudinally extending tops 104 being moved away from the skin-side surface.

Since the leakage preventing walls 103 exert the elastic contractive force to bring the front and rear ends 103a, 103b closer to each other as set forth above, the tops 104 of the leakage preventing walls 103 try to extend linearly between the front and rear ends 103a, 103b. In the deformed state shown in FIG. 14, accordingly, the main body 101 subjected to the elastic contractive force is folded at a fold boundary 105 being a boundary between front and rear portions 101A, 101B, so that at the folding boundary 105, the tops 104 of the leakage preventing walls 103 are spaced as far away from the skin-side surface of the main body 101 as possible.

When the absorbent article 100 is worn, the front portion 101A faces the lower abdomen, the crotch and the perineum, while the rear portion 101B faces the anus and the cleft of the buttocks posterior to the anus, and optionally covers the region posterior to the cleft of the buttocks. Here, the tops 104 of the leakage preventing walls 103 will be relatively strongly pressed against the wearer's body at the folding boundary 105 and forward and rearward portions thereof, giving an uncomfortable feeling to the perineum, the anus and the buttocks.

At the folding boundary 105 where the tops 104 are farthest away from the main body 101, moreover, the leakage preventing walls 103 tend to be influenced by the body pressure from adjacent the anus or from the buttocks. Therefore, the leakage preventing walls 103 subjected to the body pressure tend to fall to the skin-side surface of the main body 101. As a result, the skin-side surface of the main body 101 will be widely covered with the leakage preventing walls 103 to reduce the substantial liquid absorbing area of the main body 101, which results in causing liquid to leak laterally or obliquely rearward.

SUMMARY OF THE INVENTION

The present invention has been worked out in view of the shortcomings in the prior art set forth above. It is therefore an object of the present invention to provide an absorbent article in which leakage preventing walls in contact with the wearer's body hardly give an uncomfortable feeling and are sufficiently effective in preventing leakage.

According to the present invention, there is provided an absorbent article comprising:

an elongated main body having a skin-side surface and a garment-side surface and including a liquid absorbent layer intended to absorb liquid applied to the skin-side surface and a backsheet appearing on the garment-side surface; and leakage preventing walls disposed at equal distances on each side of a longitudinal centerline of the main body and extending longitudinally of the main body, the leakage preventing walls being fixed at longitudinally opposing front and rear ends to the main body and subjected to a longitudinal elastic contractive force so as to rise between the front and rear ends with longitudinally extending tops moved away from the skin-side surface, wherein each leakage preventing wall is provided, between the front and rear ends, with a local constraint portion in which an allowable rising height from the skin-side surface to the top is constrained to be smaller than in portions forward and rearward of the constraint portion.

In the absorbent article such as sanitary napkin, disposable diaper or urine absorbing pad, the rising of the leakage preventing walls is locally constrained at a position between the front and rear ends of each leakage preventing wall. Therefore, the tops of the leakage preventing walls can easily conform to the surface of the wearer's body, causing less uncomfortable feeling and preventing the leakage preventing walls from falling to the skin-side surface of the main body.

In the present invention, for example, the constraint portion may be located rearward of a portion that is intended to face an excretory part of the wearer's body. If the rising of the leakage preventing walls is constrained rearward of the excretory part, the tops of the leakage preventing walls on both sides of the excretory part may be generally parallel to the skin-side surface of the main body, coming into contact with the wearer's body without giving an uncomfortable feeling. In addition, even if the leakage preventing walls that are constrained in rising height rearward of the excretory part fall to the skin-side surface of the main body, they will hardly present the problem of reduction in exposed area of the skin-side surface of the main body. To this end, the constraint portion is preferably located at a midpoint between the front and rear ends of the leakage preventing wall or rearward of the midpoint.

Alternatively, the constraint portion may be located forward of the midpoint.

Also in the present invention, the absorbent article may further comprise: fold-back flaps projecting outward from transversely opposite sides of the main body and intended to be folded back against an outer surface of an undergarment at a crotch part thereof; and rear flaps located rearward of the fold-back flaps, projecting outward from the transversely opposite sides of the main body and intended to be placed on an inner surface of the undergarment in an unfolded state, providing the article with a narrow portion that is located between the fold-back flaps and the rear flaps and has a smaller width than a portion including the fold-back flaps, wherein the constraint portion may be located in the narrow portion. This absorbent article may be embodied in a sanitary napkin suitable for nighttime use. In this construction, the absorbent article tends to be folded in the narrow portion located between the fold-back flaps and the rear flaps, but because the leakage preventing walls are constrained in rising height in the narrow portion of the absorbent article, they will cause less uncomfortable feeling. In addition, even if the leakage preventing walls fall in the narrow portion, the skin-side surface of the main body will not be widely covered.

Also in the present invention, the constraint portion is preferably spaced at least ¼ of L0 apart from both the front and rear ends of the leakage preventing wall, where L0 represent a length between the front and rear ends when the main body is developed flat. With this construction, the advantages of the constraint portion can be fully exploited.

In the constraint portion, for example, the leakage preventing wall may be joined to itself so as to prevent the top from moving away from the skin-side surface as far as in the portions forward and rearward of the constraint portion.

In the constraint portion, alternatively, the leakage preventing wall may be additionally joined to the skin-side surface of the main body.

In the constraint portion, still alternatively, a constraining member may be disposed to constrain the leakage preventing wall so as not to move away from the skin-side surface.

BRIEF DESCRIPTION OF THE DRAWINGS

The present invention will be understood more fully from the detailed description given hereinafter and from the accompanying drawings of the preferred embodiments of the present invention, which, however, should not be taken to limit to the invention, but are for explanation and understanding only.

In the drawings:

FIG. 14 is a longitudinal sectional view of a conventional sanitary napkin in a free state.

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instances, well-known structures are not shown in detail in order not to obscure the features of the present invention.

It should be noted that the absorbent article, as well as its individual components, has two major surfaces: of which one surface intended to be worn toward the wearer's crotch is referred to as "skin-side surface", while the other surface is referred to as "garment-side surface". It should also be noted that unless otherwise stated, the term "length" as used herein refers to a dimension measured longitudinally of the absorbent article and the term "width" as used herein refers to a dimension measured transversely of the absorbent article.

Figure 1:
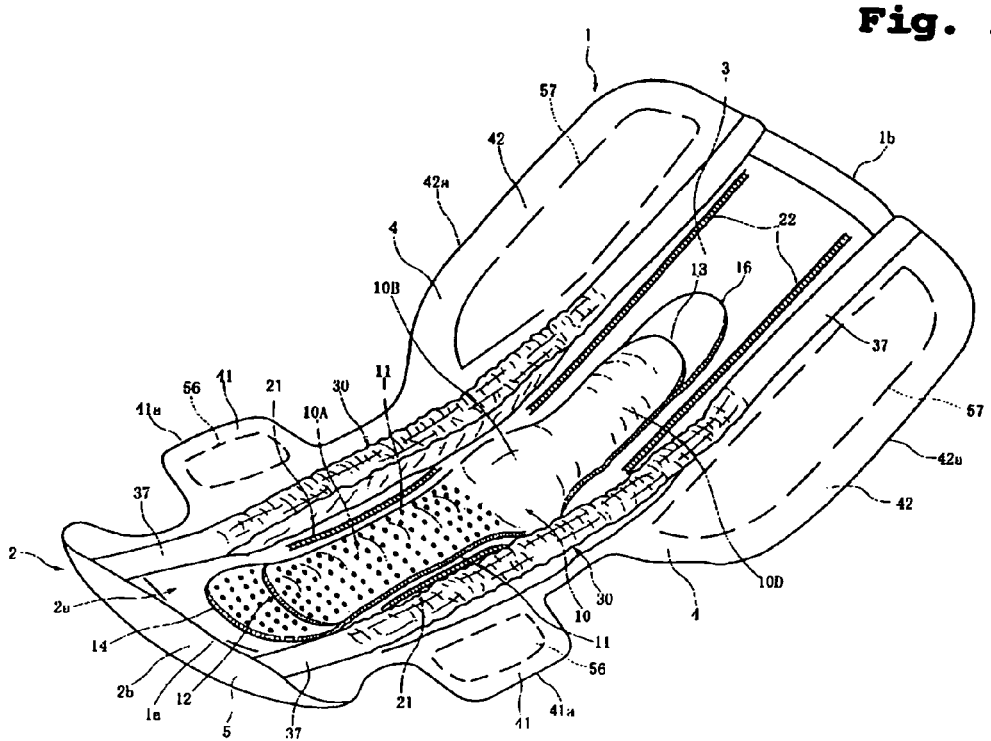
FIG. 1 is a perspective view of a sanitary napkin according to a first embodiment of the present invention.
Figure 2:
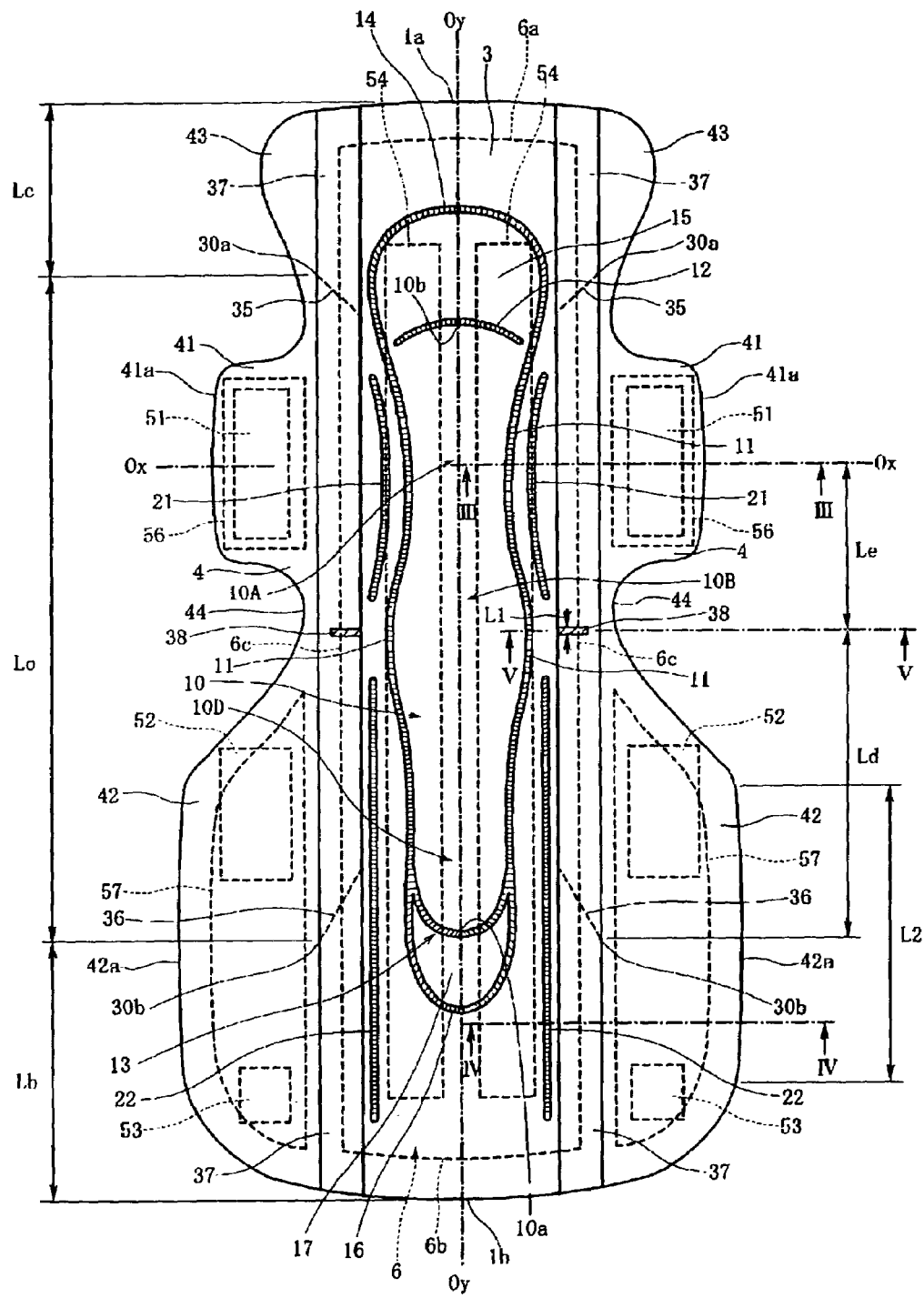
FIG. 2 is a top plan view of the sanitary napkin according to the first embodiment.
Figure 3:
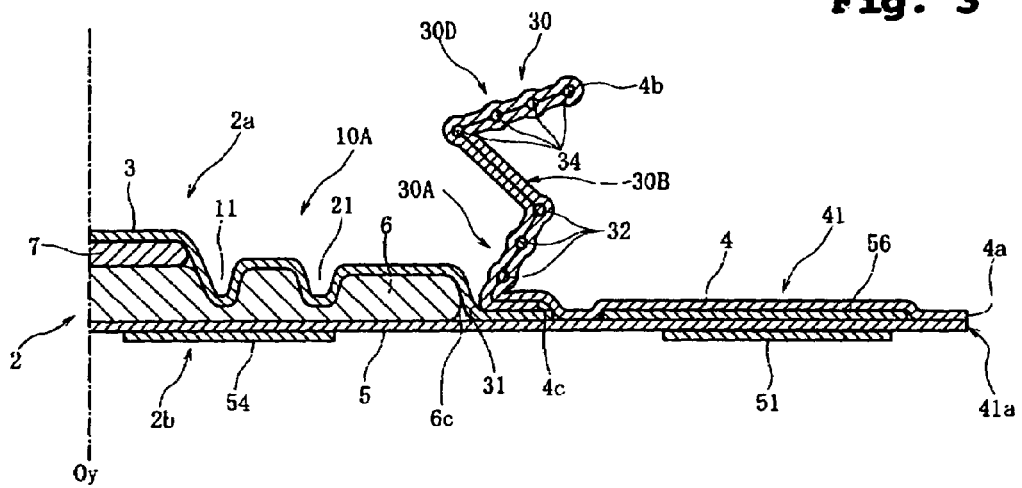
FIG. 3 is a half sectional view taken along line III-III of FIG. 2.
Figure 4:
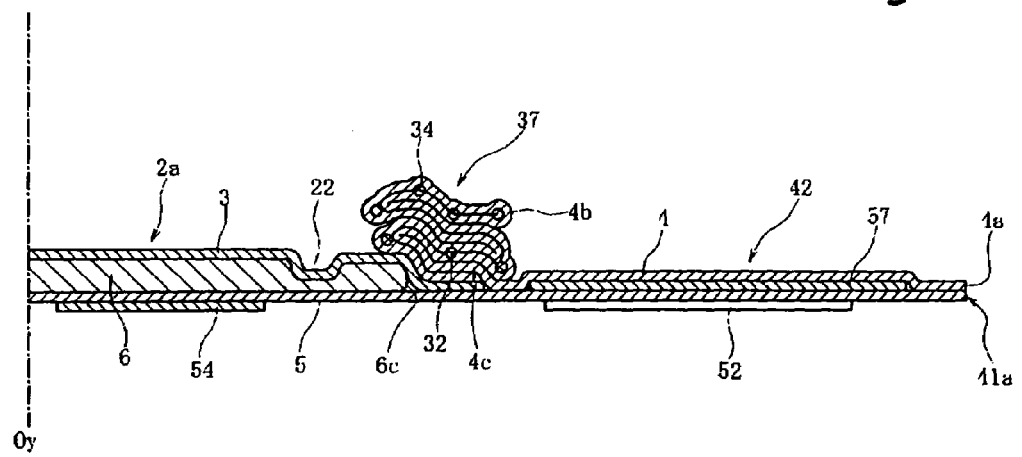
FIG. 4 is a half sectional view taken along line IV-IV of FIG. 2.
Figure 5:
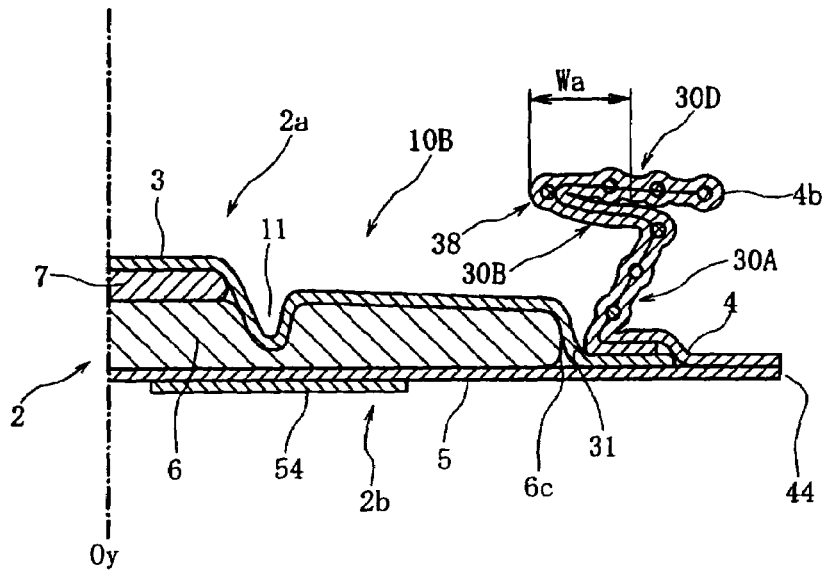
FIG. 5 is a half sectional view taken along line V-V of FIG. 2.

FIG. 1 is a perspective view of a sanitary napkin 1 according to a first embodiment of the present invention; FIG. 2 is a top plan view of the sanitary napkin 1; FIG. 3 is a half sectional view taken along line III-III of FIG. 2; FIG. 4 is a half sectional view taken along line IV-IV of FIG. 2; and FIG. 5 is a half sectional view taken along line V-V of FIG. 2.

According to the first embodiment shown in FIGS. 1-5, the sanitary napkin 1 comprises: an elongated main body 2 having a skin-side surface 2a and a garment-side surface 2b; and a pair of leakage preventing walls 30, 30 that are allowed to rise from the skin-side surface 2a of the main body 2.

In FIG. 2, the sanitary napkin 1, which is slightly curved in FIG. 1, is shown in a fully opened (or flattened) state. FIG. 2 shows a longitudinal centerline Oy-Oy coinciding with midpoints of front and rear end edges 1a, 1b of the sanitary napkin 1, wherein the sanitary napkin 1 has bilateral symmetry about the longitudinal centerline Oy-Oy.

FIG. 2 also shows a transverse reference line Ox-Ox perpendicular to the longitudinal centerline Oy-Oy. The sanitary napkin 1 is intended to be worn with the skin-side surface 2a facing the crotch of a woman so that the intersection between the longitudinal centerline Oy-Oy and the transverse reference line Ox-Ox faces the woman's vaginal opening.

As shown in FIGS. 3 and 4, a liquid-permeable topsheet 3 appears on the skin-side surface 2a of the main body 2, in a region between the leakage preventing walls 30, 30; a side sheet 4 appears outside each leakage preventing wall 30. In the present embodiment, the side sheet 4 forms the leakage preventing wall 30. On the other hand, a liquid-impermeable backsheet 5 appears on the garment-side surface 2b of the main body 2.

In the region between the leakage preventing walls 30, 30, the main body 2 has a liquid absorbent layer 6 disposed between the topsheet 3 and the backsheet 5. As shown in FIG. 2, the liquid absorbent layer 6 is of an almost rectangular shape. The liquid absorbent layer 6 has a front end edge 6a slightly inside the front end edge 1a of the sanitary napkin 1 and a rear end edge 6b slightly inside the rear end edge 1b of the sanitary napkin 1. The liquid absorbent layer 6 has transversely opposite side edges 6c inside rising bases 31 of the leakage preventing walls 30.

In the skin-side surface 2a, compressed grooves where the topsheet 3 and the liquid absorbent layer 6 are compressed are formed in the region between the leakage preventing walls 30, 30. As shown in FIG. 2, the compressed grooves comprise: longitudinal compressed grooves 11, 11 extending longitudinally in a curved manner; a front transverse compressed groove 12 located between front portions of the longitudinal compressed grooves 11, 11; and a rear transverse compressed groove 13 connecting rear portions of the longitudinal compressed grooves 11, 11.

The region surrounded by the longitudinal compressed grooves 11, 11, the front transverse compressed groove 12, and the rear transverse compressed groove 13 is referred to as elongated main absorbent region 10. The main absorbent region 10 includes a front main absorbent region 10A, an intermediate main absorbent region 10B, and a rear main absorbent region 10D. The main absorbent region 10 has a length of 150 to 300 mm as measured from a front end 10b to a rear end 10a. For instance, the main body 2 may have a length of 180 to 380 mm.

In the front main absorbent region 10A, the right and left longitudinal compressed grooves 11, 11 are curved toward the longitudinal centerline Oy-Oy, wherein the distance between the longitudinal compressed grooves 11, 11 is smallest on the transverse reference line Ox-Ox. In the intermediate main absorbent region 10B, the longitudinal compressed grooves 11, 11 are curved away from the longitudinal centerline Oy-Oy. The rear main absorbent region 10D is elongated longitudinally of the napkin so that the distance between the longitudinal compressed grooves 11, 11 is smaller than in the intermediate main absorbent region 10B.

In the main absorbent region 10, a bulky, liquid permeable layer (cushion layer) 7 of a lower density than the liquid absorbent layer 6 is disposed between the topsheet 3 and the liquid absorbent layer 6, as shown in FIGS. 3 and 5. As a result, the skin-side surface 2a of the main body 2 is raised more in the main absorbent region 10 than in the surrounding region, as shown in FIG. 1.

As shown in FIG. 2, the compressed grooves further comprise: a first outside transverse compressed groove 14; a second outside transverse compressed groove 16; first outside longitudinal compressed grooves 21, 21; and second outside longitudinal compressed grooves 22, 22.

The first outside transverse compressed groove 14 is disposed forward of the front transverse compressed groove 12. The first outside transverse compressed groove 14 is curved forward and connects the right and left longitudinal compressed grooves 11, 11. The region surrounded by the front transverse compressed groove 12 and the first outside transverse compressed groove 14 is referred to as forward diffusion suppressing region 15.

The second outside transverse compressed groove 16 is disposed rearward of the rear transverse compressed groove 13. The longitudinal compressed grooves 11, 11, the rear transverse compressed groove 13, and the second outside transverse compressed groove 16 are connected together, and both the rear transverse compressed groove 13 and the second outside transverse compressed groove 16 are curved rearward. Here, the region surrounded by the rear transverse compressed groove 13 and the second outside transverse compressed groove 16 is referred to as rearward diffusion suppressing region 17.

On both right and left sides of the front main absorbent region 10A, the first outside longitudinal compressed grooves 21, 21 are disposed at a distance outwardly apart from the longitudinal compressed grooves 11, 11. The first outside longitudinal compressed grooves 21, 21 are also curved toward the longitudinal centerline Oy-Oy, wherein the distance therebetween is smallest on the transverse reference line Ox-Ox.

On both right and left sides of the rear main absorbent region 10D, the second outside longitudinal compressed grooves 22, 22 are disposed at a distance transversely apart from the longitudinal compressed grooves 11, 11. The second outside longitudinal compressed grooves 22, 22 extend longitudinally in substantially parallel relation to the longitudinal centerline Oy-Oy, wherein rear ends are located farther rearward than the second outside transverse compressed groove 16.

The individual compressed grooves are formed by heating the topsheet 3 and the liquid absorbent layer 6 under pressure from the side of the topsheet 3. At the bottoms of the individual compressed grooves, high-density compressed portions (highly compressed portions) and medium-density compressed portions (portions whose density is slightly lower than the high-density compressed portions) alternate with each other along the linear pattern of the compressed grooves so that the grooves are of a sufficient depth overall. The individual compressed grooves may be replaced by dot-like compressed portions arranged along the linear pattern at spaced intervals.

As shown in FIGS. 3 to 5, the side sheet 4 has an edge 4a coinciding with the outer edge of the backsheet 5. The side sheet 4 has a single-layer portion and a multi-layer portion, wherein the single-layer portion is bonded to the backsheet 5 or other materials disposed on the backsheet 5, whereas the multi-layer portion forms the leakage preventing wall 30 (see FIGS. 3 and 5) or a stacked/fixed portion 37 (see FIG. 4). In the multi-layer portion, at first, the side sheet 4 is folded on a fold line 4b to have an edge 4c on the topsheet 3. In FIGS. 3 and 5, the side sheet 4 is bonded to the topsheet 3 from the rising base 31 to the edge 4c.

Confronting surfaces of the side sheet 4 thus folded in two are bonded together through a hot-melt type adhesive with a plurality of elastic members 32, 34 disposed therebetween. The individual elastic members 32, 34 extend longitudinally over the entire length of the leakage preventing wall 30 and beyond the front and rear ends 30a, 30b. The elastic members 32, 34 are bonded to the side sheet 4 while being longitudinally stretched to a predetermined degree.

In an area of a length Lb from a rear bond edge 36 to the rear end edge 1b (see FIG. 2), the multi-layer portion of the side sheet 4 previously folded in two is further folded in three, as shown in FIG. 4, wherein these layers are bonded to each other as well as to the topsheet 3, thereby forming the stacked/fixed portion 37. Also in an area of a length Lc from a front bond edge 35 to the front end edge 1a, the multi-layer portion of the side sheet 4 is similarly folded and bonded, forming the stacked/fixed portion 37.

The front bond edge 35 and the rear bond edge 36 extend obliquely with respect to both the longitudinal direction and the transverse direction. Between the front bond edge 35 and the rear bond edge 36, the multi-layer portion of the side sheet 4 previously folded in two forms the leakage preventing wall 30 that can rise from the skin-side surface 2a, as shown in FIGS. 3 and 5. It should be noted that the front end 30a of the leakage preventing wall 30 refers to one end of the front bond edge 35 that is closer to the front end edge 1a, and the rear end 30b of the leakage preventing wall 30 refers to one end of the rear bond edge 36 that is closer to the rear end edge 1b. The length of the leakage preventing wall 30 from the front end 30a to the rear end 30b is indicated by L0.

The length L0 is at least ⅘ the length of the main absorbent region 10. Preferably, the length L0 is equal to or greater than the length of the main absorbent region 10. Also preferably, the front end 30a is located forward of the front end 10b of the main absorbent region 10 and the rear end 30b is located rearward of the rear end 10a of the main absorbent region 10.

The elastic members 32, 34 exert an elastic contractive force between the front end 30a and the rear end 30b, so that an elastic force acts to bring the front end 30a and the rear end 30b closer to each other, whereby the main body 2 is curved as shown in FIG. 1 and each leakage preventing wall 30 is raised from the skin-side surface 2a between the front end 30a and the rear end 30b.

Because the side sheet 4 at the stacked/fixed portion 37 is folded in a multi-layer structure and then bonded and fixed as shown in FIG. 4, the leakage preventing wall 30 includes: a lower inclined panel 30A extending obliquely upward from the rising base 31 toward the outside; an intermediate inclined panel 30B extending obliquely upward from the upper end of the lower inclined panel 30A toward the longitudinal centerline Oy-Oy; and a skin-contacting panel 30D extending obliquely upward from the upper end of the intermediate inclined panel 30B toward the outside, as shown in the half sectional view of FIG. 3. Here, the free end of the skin-contacting panel 30D coinciding with the fold line 4b is referred to as top of the leakage preventing wall 30.

As shown in FIG. 2, each leakage preventing wall 30 is provided, between the front and rear ends 30a, 30b, with a single local constraint portion 38. If necessary, each leakage preventing wall 30 may have two or more constraint portions between the front and rear ends 30a, 30b. In the constraint portion 38, a distance from the rising base 31 to the top 4b when the leakage preventing wall 30 is forcibly developed (i.e., allowable rising height) is constrained to be smaller than in portions forward and rearward of the constraint portion 38.

In the constraint portion 38, the intermediate inclined panel 30B and the skin-contacting panel 30D are joined to each other such as by adhesive-bonding or fusion-bonding, as shown in FIG. 5. In FIG. 5, Wa represents a width of the join that provides the constraint portion 38. In the constraint portion 38, the allowable rising height from the rising base 31 to the top 4b is reduced by 2×Wa. On the other hand, a length L1 of the constraint portion 38 (i.e., a length of the join) is equal to or less than 20 mm, preferably equal to or less than 5 mm.

Along the transverse reference line Ox-Ox, fold-back flaps 41 are disposed to project transversely outward from the main body 2. Each fold-back flap 41 extends over a given length with center at the transverse reference line Ox-Ox. Rearward of the fold-back flaps 41 are disposed rear flaps 42 also projecting transversely outward from the main body 2; forward of the fold-back flaps 41 are disposed front flaps 43 projecting transversely outward from the main body 2. Since the sanitary napkin 1 has bilateral symmetry about the longitudinal centerline Oy-Oy, the right and left flaps are of symmetrical shape.

The fold-back flap 41 has a side edge 41a that is gently curved transversely outward, wherein the half-width from the longitudinal centerline Oy-Oy to the side edge 41a of the fold-back flap 41 is largest on the transverse reference line Ox-Ox.

The rear flap 42 provides an almost constant half-width within the area of a length L2. That is, the rear flap 42 in this area has a side edge 42a that is substantially parallel to the longitudinal centerline Oy-Oy. Of course, the side edge 42a may be parallel to the longitudinal centerline Oy-Oy without any deviation.

The width between the side edges 42a, 42a of the rear flaps 42, 42 is larger than the width between the side edges 41a, 41a of the fold-back flaps 41, 41. The length of the rear flap 42 is larger than the length of the fold-back flap 41. Between the fold-back flaps 41 and the rear flaps 42, the sanitary napkin 1 has a narrow portion whose side edges are indicated by 44, 44.

In the sanitary napkin 1, front pressure-sensitive adhesive layers 51, first rear pressure-sensitive adhesive layers 52, second rear pressure-sensitive adhesive layers 53, and central pressure-sensitive adhesive layers 54 are disposed on the garment-side surface, as shown in FIG. 2. In the fold-back flap 41, the front pressure-sensitive adhesive layer 51 is disposed on the backsheet 5. In the rear flap 42, the first and second rear pressure-sensitive adhesive layers 52, 53 longitudinally spaced apart from each other are disposed on the backsheet 5. In the region between the leakage preventing walls 30, the central pressure-sensitive adhesive layers 54 given the shape of a longitudinally extending strip are disposed on the backsheet 5.

In the fold-back flap 41, as shown in FIGS. 2, 3 and 4, a reinforcing sheet 56 is interposed between and bonded to the backsheet 5 and the side sheet 4. Also in the rear flap 42, a reinforcing sheet 57 is interposed between and bonded to the backsheet 5 and the side sheet 4.

In the sanitary napkin 1, the constraint portions 38 of the leakage preventing walls 30 are located on both sides of the intermediate main absorbent region 10B. In addition, the constraint portions 38 are located in the narrow portion between the fold-back flaps 41 and the rear flaps 42. More specifically, the sentence "the constraint portions 38 are located in the narrow portion" means that the constraint portions 38 are located in a portion which is provided between the fold-back flaps 41 and the rear flaps 42 and whose width between the side edges is smaller, preferably at least 5 mm smaller, than the width between the side edges 41a, 41a of the fold-back flaps 41, 41.

Accordingly, because the constraint portions 38 are not located between the front main absorbent region 10A and the side edges 41a of the fold-back flaps 41, the tops 4b on both sides of the front main absorbent region 10A can relatively freely move away from the skin-side surface 2a. Similarly, because the constraint portions 38 are not located between the rear main absorbent region 10D and the side edges 42a of the rear flaps 42, the tops 4b on both sides of the rear main absorbent region 10D can relatively freely move away from the skin-side surface 2a.

In the sanitary napkin 1, the constraint portion 38 is located near the midpoint of the length L0 of the leakage preventing wall 30. In the embodiment shown in FIG. 2, an additional constraint portion may be provided between the constraint portion 38 and the rear end 30b of the leakage preventing wall 30.

Next, preferred examples of the individual components of the sanitary napkin 1 will be described.

The topsheet 3 is a liquid-permeable sheet, such as a through-air bonded nonwoven fabric, a spunlaced nonwoven fabric, or an apertured resin film (resin film formed with a large number of liquid passage holes). The backsheet 5 is a resin film that is impermeable to liquid but may be breathable.

The liquid absorbent layer 6 may be a layer of pulp, a layer of pulp and superabsorbent polymer, or an air-laid nonwoven fabric in which only pulp or pulp and rayon are deposited by air-laid process and the fibers are fixed together through an adhesive. The liquid permeable layer 7 is a bulky nonwoven fabric of a three-dimensional network structure, such as a through-air bonded nonwoven fabric or an air-laid nonwoven fabric in which pulp and synthetic fibers are deposited by air-laid process and the fibers are fixed together through an adhesive.

The side sheet 4 is impermeable to liquid and is preferably treated to be water-repellent. The side sheet 4 may be a meltblown nonwoven fabric, a spunbonded nonwoven fabric, or a laminated composite of spunbond/meltblown/spunbond.

The reinforcing sheets 56, 57 may be of a spunbonded nonwoven fabric, a point-bonded nonwoven fabric, a meltblown nonwoven fabric, or a paper material. The pressure-sensitive adhesive layers 51, 52, 53 and 54 may be of a rubber-based hot-melt type adhesive.

Figure 12:
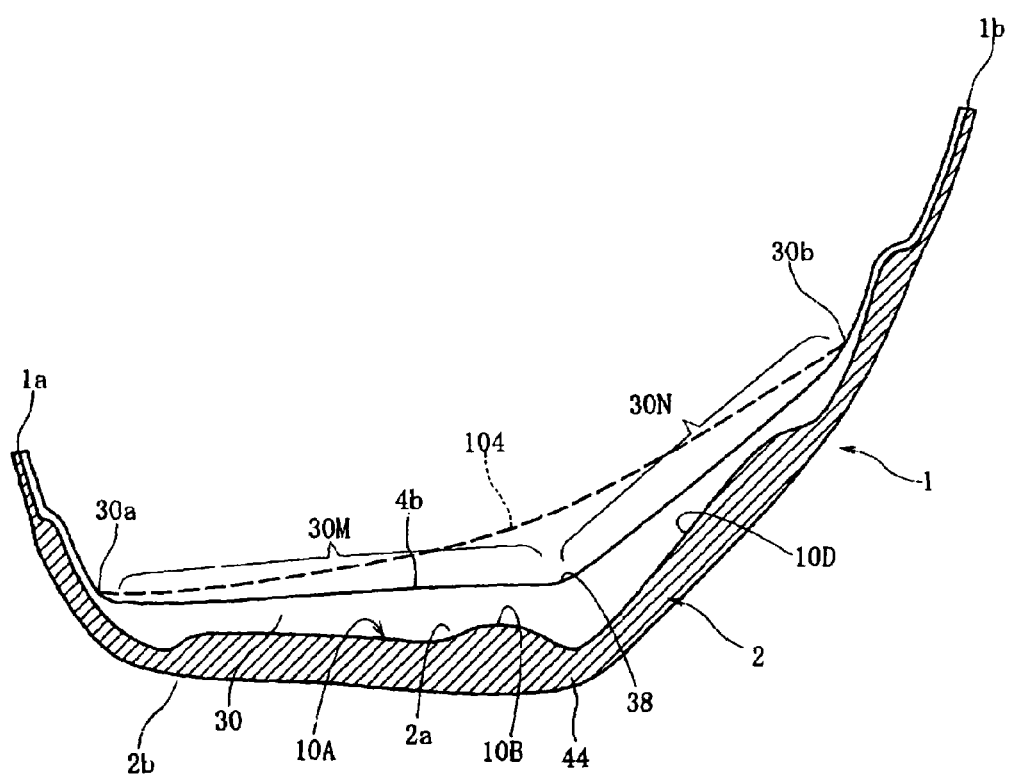
FIG. 12 is a longitudinal sectional view of a sanitary napkin in a free state.

FIG. 12 is a longitudinal sectional view taken along the longitudinal centerline Oy-Oy, wherein the sanitary napkin 1 is in a free state where no external force is exerted as shown in FIG. 1.

In the leakage preventing wall 30, the longitudinally extending elastic members 32, 34 are fixed through an adhesive while being longitudinally stretched. In the free state, accordingly, the elastic contractive force of the elastic members 32, 34 bring the front and rear ends 30a, 30b of the leakage preventing walls 30 closer to each other, whereby the main body 2 of the sanitary napkin 1 is deformed so that the skin-side surface 2a can be recessed. Between the front and rear ends 30a, 30b, consequently, the leakage preventing walls 30 are raised with the tops 4b moved away from the skin-side surface 2a.

As shown in FIG. 5, the allowable rising height from the skin-side surface 2a to the top 4b is constrained in the constraint portion 38. As shown in FIG. 12, accordingly, the top 4b of the leakage preventing wall 30 is folded at a boundary between front and rear portions 30M, 30N, wherein the front portion 30M is a portion from the front end 30a to the constraint portion 38 and the rear portion 30N is a portion from the constraint portion 38 to the rear end 30b.

It should be noted that in FIG. 12, the top 104 of the conventional leakage preventing wall in which the constraint portion 38 is not provided is shown with a dotted line for comparison.

When the elastic contractive force of the elastic members 32, 34 is exerted on the sanitary napkin 1, the main body 2 tends to be folded in the narrow portion located between the fold-back flaps 41 and the rear flaps 42 as shown in FIG. 12. In the narrow portion having the side edges 44, 44, the leakage preventing walls 30 are constrained in allowable rising height with the constraint portions 38.

The sanitary napkin 1 is to be placed on an inner surface of an undergarment with the skin-side surface 2a being directed toward the wearer's body. Then, the fold-back flaps 41 projecting into the leg openings of the undergarment may be folded back against an outer surface of the crotch part and adhered thereto through the front pressure-sensitive adhesive layers 51 disposed on the fold-back flaps 41. In addition, the garment-side surface 2b of the main body 2 of the sanitary napkin 1 is adhered to the inner surface of the undergarment, from the crotch part to the lower part of the back body, through the central pressure-sensitive adhesive layers 54. Furthermore, the rear flaps 42 in a developed state are placed on the inner surface of the undergarment at the lower part of the back body and their garment-side surfaces are adhered to the inner surface of the undergarment through the first rear pressure-sensitive adhesive layers 52 and the second rear pressure-sensitive adhesive layers 53.

When worn, the longitudinal central portion of the front main absorbent region 10A, i.e., the intersection of the longitudinal centerline Oy-Oy and the transverse reference line Ox-Ox and its surrounding area may confront the woman's vaginal opening. On the other hand, the intermediate portion between the front main absorbent region 10A and the intermediate main absorbent region 10B may confront the perineum, and the front portion of the intermediate main absorbent region 10B may confront the anus. Accordingly, the rear main absorbent region 10D may extend along the cleft of the buttocks.

In the sanitary napkin 1, since the leakage preventing walls 30 are constrained in allowable rising height on both sides of the intermediate main absorbent region 10B, the angle of inclination of the top 4b of the leakage preventing wall 30 in the front portion 30M may be smaller than that of the top 104 of the conventional leakage preventing wall, as shown in FIG. 12. Here, it is possible to make the top 4b of the leakage preventing wall 30 in the front portion 30M extend generally parallel with the skin-side surface 2a of the main body 2 by further constraining the allowable rising height in the constraint portion 38.

Since the top 4b of the leakage preventing wall 30 is gently inclined in the front portion 30M, the skin-contacting panels 30D of the leakage preventing walls 30 brought in contact with the wearer's body on both sides of the vaginal opening and the perineum may provide less irritation. Also in the rear portion 30N, the top 4b of the leakage preventing wall 30 may extend generally parallel with the skin-side surface 2a of the main body 2, reducing the irritation to both sides of the anus and the buttocks.

Here, the rising height of the top 104 that is not constrained by the constraint portion 38 will be largest in the narrow portion having the side edges 44, 44; but in this embodiment, the allowable rising height of the leakage preventing walls 30 is constrained with the constraint portions 38 provided in the narrow portion. Therefore, even if the leakage preventing walls 30 in this portion fall to the skin-side surface 2a due to the body pressure, the skin-side surface 2a will not be widely covered with the leakage preventing walls 30.

The constraint portions 38 may be located farther rearward than in FIG. 2. More specifically, the constraint portions 38 may be located between the rear main absorbent region 10D and the side edges 42a of the rear flaps 42.

However, a length Ld between the constraint portion 38 and the rear end 30b (over which rising of the leakage preventing wall 30 is not constrained) need be at least ¼, preferably at least ⅓ of the length L0 of the leakage preventing wall 30. In other words, the length Ld need be equal to or greater than 45 mm. With the constraint portion 38 being thus spaced forward from the rear end 30b, rising of the leakage preventing wall 30 can be controlled as shown in FIG. 12, so that the top 4b can easily conform to the shape from the crotch to the buttocks.

On the other hand, a length Le between the transverse reference line Ox-Ox and the constraint portion 38 (over which rising of the leakage preventing wall 30 is not constrained) is preferably equal to or less than 95 mm. The constraint portion 38 may be located forward of the midpoint of the length L0 of the leakage preventing wall 30. Here, a length between the constraint portion 38 and the front end 30a (over which rising of the leakage preventing wall 30 is not constrained) is preferably equal to or greater than 45 mm.

Figure 13:
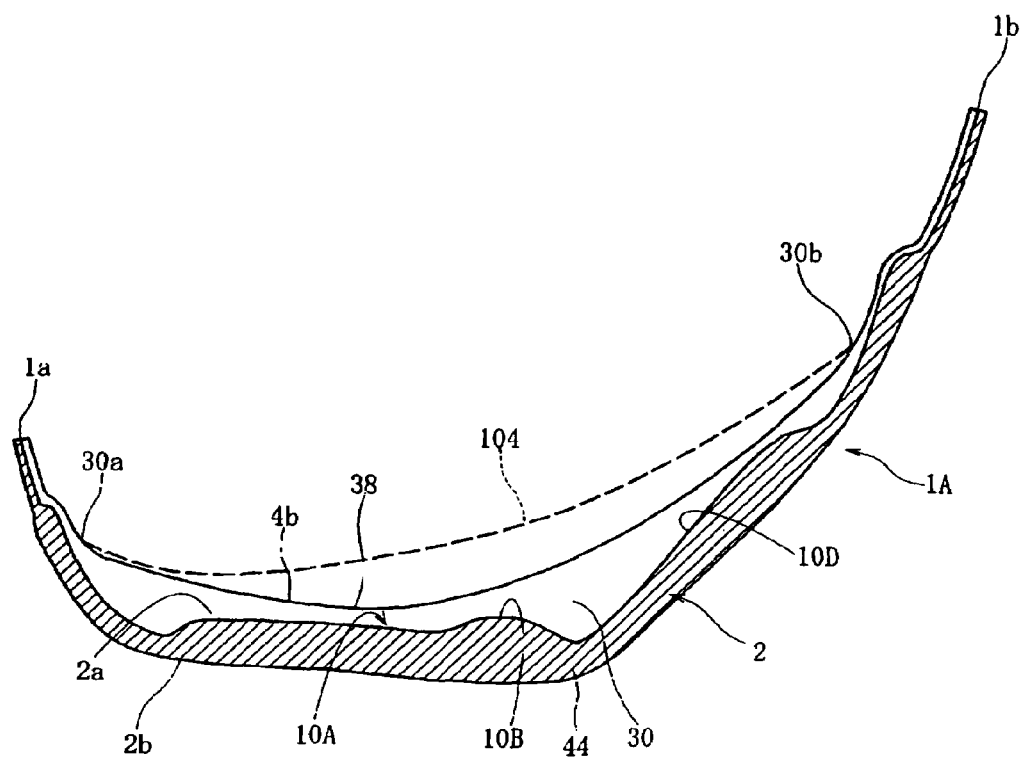
FIG. 13 is a longitudinal sectional view of another sanitary napkin in a free state.

FIG. 13 is a longitudinal sectional view of a sanitary napkin 1A according to a second embodiment of the present invention, wherein the constraint portion 38 is located forward of the midpoint of the length L0 of the leakage preventing wall 30 and adjacent the transverse reference line Ox-Ox. Also in FIG. 13, the top 104 of the conventional leakage preventing wall is shown for comparison with the top 4b of the leakage preventing wall 30.

In the sanitary napkin 1A shown in FIG. 13, since the allowable rising height of the leakage preventing wall 30 is constrained in the constraint portion 38 on both sides of the front main absorbent region 10A, the top 4b of the leakage preventing wall 30 is prevented from abruptly ascending rearward on both sides of the front main absorbent region 10A that is intended to face the vaginal opening, reducing the irritation to both sides of the vaginal opening. With the constraint portion 38 being spaced at least 45 mm apart from the front end 30a of the leakage preventing wall 30, moreover, the allowable rising height of the leakage preventing wall 30 can be appropriately controlled on both sides of the intermediate and rear main absorbent region 10B, 10D, reducing the irritation to the buttocks as well as preventing the skin-side surface 2a of the main body 2 from being widely covered with the fallen leakage preventing walls 30.

FIGS. 6 to 11 show different constraint portions according to other embodiments.

Figure 6:
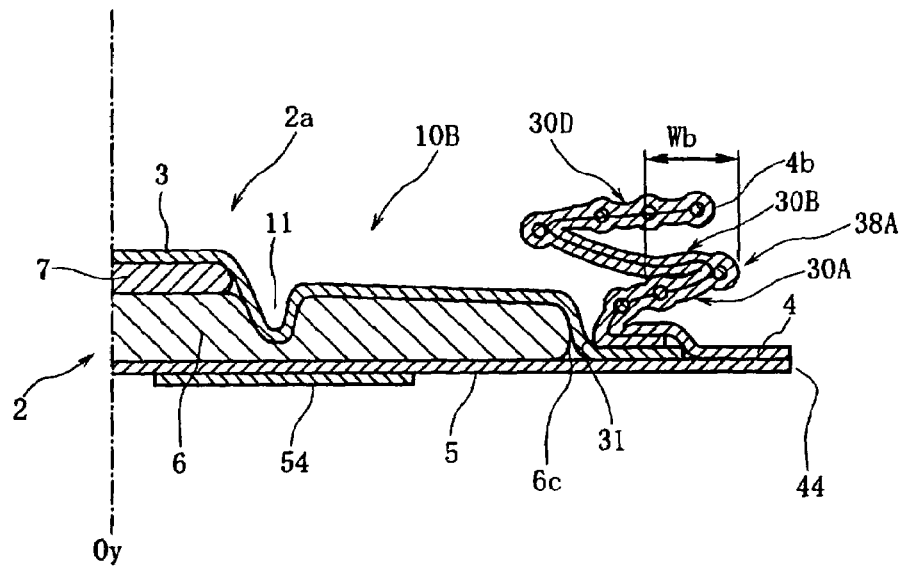
FIG. 6 is a half sectional view showing a constraint portion according to a second embodiment.

FIG. 6 shows a constraint portion 38A according to a second embodiment, in which the lower inclined panel 30A and the intermediate inclined panel 30B of the leakage preventing wall 30 are joined to each other. Thus, the allowable rising height of the leakage preventing wall 30 from the rising base 31 to the top 4b is constrained.

Figure 7:
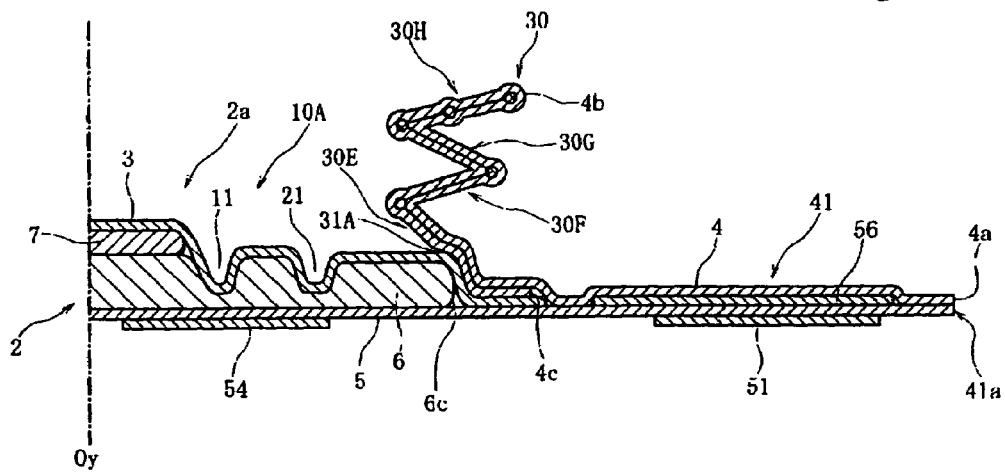
FIG. 7 is a half sectional view showing a leakage preventing wall according to a third embodiment.
Figure 8:
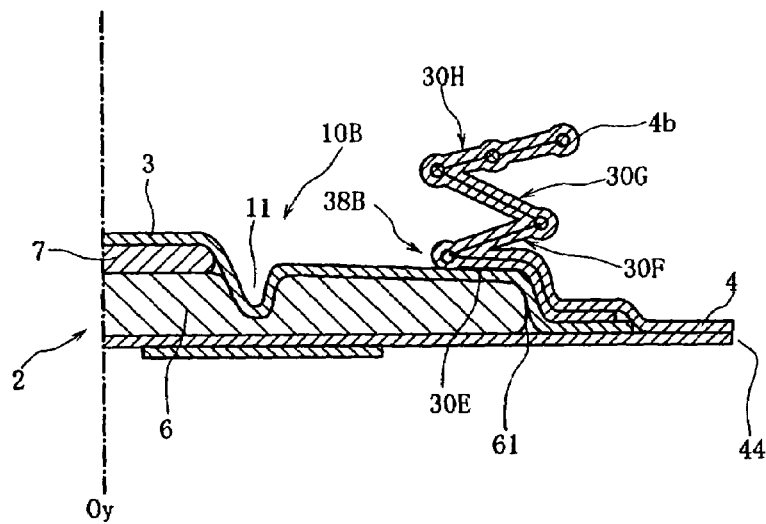
FIG. 8 is a half sectional view showing a constraint portion according to the third embodiment.

FIGS. 7 and 8 show a third embodiment. FIG. 7 is a view corresponding to the half sectional view taken along line III-III of FIG. 2, showing a portion of the leakage preventing wall 30 in which rising is not constrained. FIG. 8 is a view corresponding to the half sectional view taken along line V-V of FIG. 2, showing a constraint portion 38B provided in the leakage preventing wall 30.

In the third embodiment, the leakage preventing wall 30 exclusive of the constraint portion 38B has a rising base 31A over the liquid absorbent layer 6 as shown in FIG. 7 and includes: a lower inclined panel 30E extending obliquely upward from the rising base 31A toward the longitudinal centerline Oy-Oy; a first intermediate inclined panel 30F extending obliquely upward from the upper end of the lower inclined panel 30E toward the outside; a second intermediate inclined panel 30G extending obliquely upward from the upper end of the first intermediate inclined panel 30F toward the longitudinal centerline Oy-Oy; and a skin-contacting panel 30H extending obliquely upward from the upper end of the second intermediate inclined panel 30G toward the outside.

In the constraint portion 38B, furthermore, the lower inclined panel 30E is laid on the skin-side surface 2a and joined to the topsheet 3 as shown in FIG. 8. Thus, the allowable rising height from the skin-side surface 2a to the top 4b is constrained.

Figure 9:
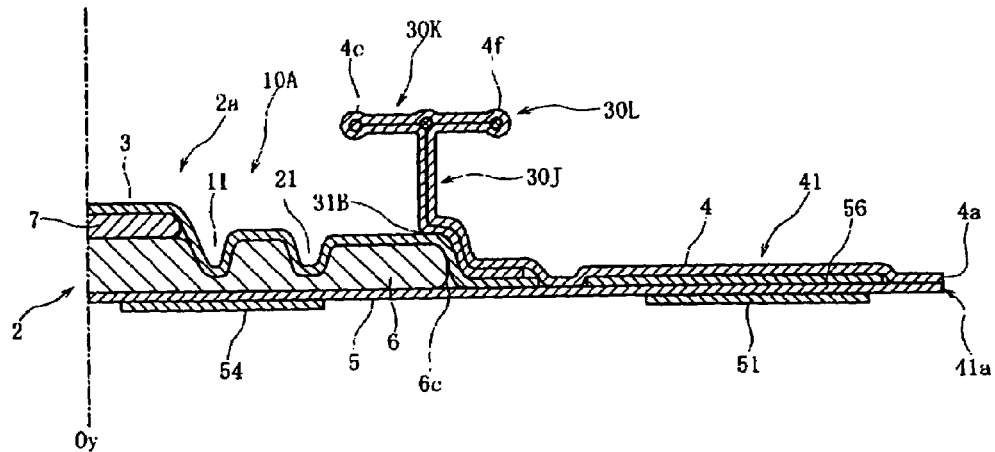
FIG. 9 is a half sectional view showing a leakage preventing wall according to a fourth embodiment.
Figure 10:
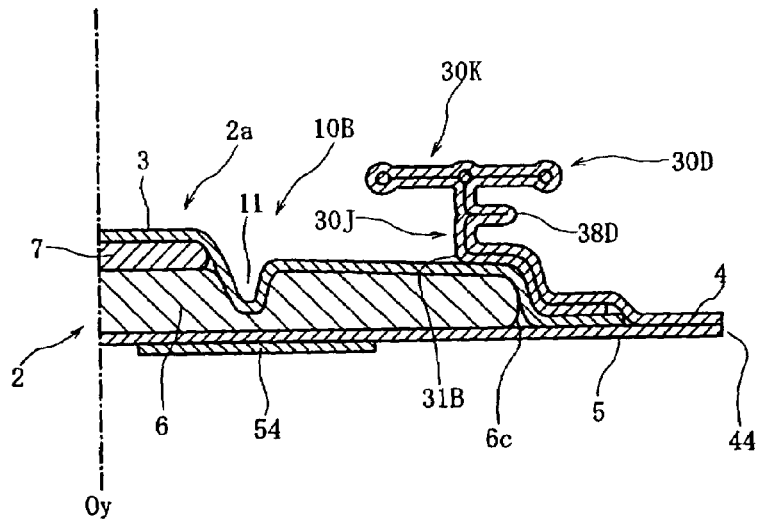
FIG. 10 is a half sectional view showing a constraint portion according to the fourth embodiment.

FIGS. 9 and 10 show a fourth embodiment. FIG. 9 is a half sectional view corresponding to the view taken along line III-III of FIG. 2, showing a portion of a leakage preventing wall 30L in which rising is not constrained. FIG. 10 is a half sectional view corresponding to the view taken along line V-V of FIG. 2, showing a constraint portion 38D provided in the leakage preventing wall 30L.

In the fourth embodiment, the leakage preventing wall 30L exclusive of the constraint portion 38D has a rising base 31B over the liquid absorbent layer 6 as shown in FIG. 9 and includes: a rising panel 30J extending substantially vertically upward from the rising base 31B; and a skin-contacting panel 30K projecting on either side from the upper end of the rising panel 30J. The left and right side edges of the skin-contacting panel 30K are indicated by 4e and 4f, respectively, and in the present embodiment, one of the side edges 4e, 4f that is allowed to move farthest away from the skin-side surface 2a is regarded as the top of the leakage preventing wall 30L.

In the constraint portion 38D, furthermore, the sheet forming the rising panel 30J is further joined to itself to have a folded portion as shown in FIG. 10. Thus, the allowable rising height from the rising base 31B to the top 4e or 4f is constrained.

Figure 11:
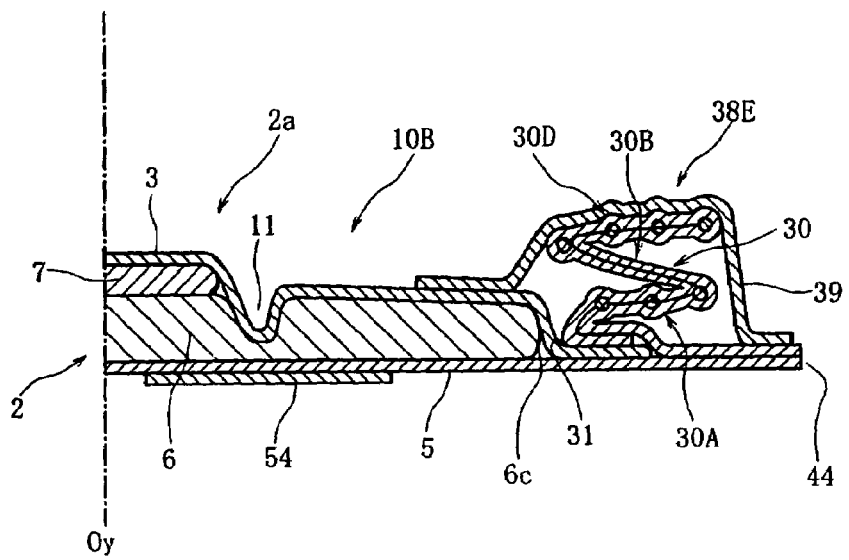
FIG. 11 is a half sectional view showing a constraint portion according to a fifth embodiment.

FIG. 11 is a half sectional view showing a constraint portion 38E according to a fifth embodiment.

In the fifth embodiment, the leakage preventing wall 30 exclusive of the constraint portion 38E has the same construction as shown in FIG. 3. The constraint portion 38E is provided with a constraining sheet 39 as a constraining member. The constraining sheet 39 is disposed to extend across the leakage preventing wall 30 from over the liquid absorbent layer 6 to adjacent the side edge of the main body 2, so that the leakage preventing wall 30 is constrained by the constraining sheet 39 for constraint of the allowable rising height of the leakage preventing wall 30. In the absorbent article of the present invention, the different constraint portions of the foregoing embodiments may be employed in combination.

The absorbent article of the present invention should not be construed as limited to a sanitary napkin, but may be embodied in a disposable diaper, urine-absorbing pad or the like as long as intended to face the crotch and the lower part of the buttocks during wear.

According to the present invention, as has been described hereinabove, since the leakage preventing wall is locally constrained in allowable rising height, the leakage preventing wall can easily conform to a curved surface of the wearer's body. In addition, since the rising height of the leakage preventing wall is constrained, the absorbent region will not be widely covered with the leakage preventing wall falling to the skin-side surface of the main body.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but to include all possible embodiments which can be embodied within a scope encompassed and equivalent thereof with respect to the features set out in the appended claims.

What is claimed is:

1. An absorbent article comprising:
    an elongated main body having a skin-side surface and a garment-side surface and including a liquid absorbent layer intended to absorb liquid applied to the skin-side surface and a backsheet appearing on the garment-side surface; and
    leakage preventing walls disposed at equal distances on each side of a longitudinal centerline of the main body and extending longitudinally of the main body, the leakage preventing walls being fixed at longitudinally opposing front and rear ends to the main body and subjected to a longitudinal elastic contractive force between the front and rear ends so as to rise between the front and rear ends with longitudinally extending tops moved away from the skin-side surface;
    wherein each leakage preventing wall is provided, between the front and rear ends, with a constraint portion in which the leakage preventing wall is capable to rise to an allowable rising height from the skin-side surface,
    the allowable rising height within the constraint portion being constrained to be smaller than the allowable rising heights in portions forward and rearward of the constraint portion;
    wherein each leakage preventing wall comprises a rising base extending longitudinally along an entire length of the leakage preventing wall along the skin side surface of the main body;
    wherein each leakage preventing wall comprises a first inclined panel extending obliquely upward from the rising base, a second inclined panel extending obliquely upward from the first inclined panel in an opposing direction to the first inclined panel, and a skin-contacting panel extending obliquely upward from the second inclined panel in an opposing direction to the second inclined panel;
    wherein said skin-contacting panel comprises a fold line, said fold line forming a top of the leakage preventing wall;
    wherein the allowable rising height is a distance between the rising base of the leakage preventing wall and the fold line of the skin contacting panel when the leakage preventing wall is forcibly developed;
    wherein in the constraint portion, one of the inclined panels is at least partially joined to an adjacent panel comprising the leakage preventing wall, thereby constraining the allowable rising height within the constraint portion; and
    wherein in the constraint portion, the leakage preventing wall is joined to itself so as to constrain the allowable rising height within the constraint portion.

2. An absorbent article according to claim 1, wherein the constraint portion is located rearward of a portion that is intended to face an excretory part of a wearer's body.

3. An absorbent article according to claim 1, wherein the constraint portion is located at a midpoint between the front and rear ends of the leakage preventing wall or rearward of the midpoint.

4. An absorbent article according to claim 1, wherein the constraint portion is located forward of a midpoint between the front and rear ends of the leakage preventing wall.

5. An absorbent article according to claim 1, wherein the constraint portion is spaced at least ¼ of L0 apart from both the front and rear ends of the leakage preventing wall, where L0 represent a length between the front and rear ends when the main body is developed flat.

6. An absorbent article according to claim 1, wherein in the constraint portion, the leakage preventing wall is additionally joined to the skin-side surface of the main body.

7. An absorbent article according to claim 1, further comprising:
    fold-back flaps projecting outwardly from transversely opposite sides of the main body and configured to be folded back against an outer surface of an undergarment at a crotch part thereof.

8. An absorbent article according to claim 7, further comprising:
    rear flaps located rearward of the fold-back flaps, projecting outwardly from the transversely opposite sides of the main body and configured to be placed on an inner surface of the undergarment in an unfolded state, providing the article with a narrow portion that is located between the fold-back flaps and the rear flaps and has a smaller width than a portion including the fold-back flaps.

9. An absorbent article according to claim 8, wherein the constraint portion is positioned within the narrow portion.

10. An absorbent article according to claim 8,
    wherein the liquid absorbent layer is recessed together with the topsheet to have a pair of longitudinal compressed grooves, a pair of first outside compressed grooves, and a pair of second outside compressed grooves on the skin-side surface of the main body, the longitudinal compressed grooves defining a main absorbent region therebetween, the first outside compressed grooves being disposed on both sides of the main absorbent region at a forward side from a line connecting the constraint portions, and the second outside compressed grooves being disposed on both sides of the main absorbent region at a rear side from the line connecting the constraint portions, and
    wherein first and second outside compressed grooves on each side of the main absorbent region are discontinuous with respect to one another in the narrow portion.

11. An absorbent article according to claim 1, wherein each leakage preventing wall has a free end disposed laterally outward, extending perpendicularly away from the longitudinal centerline of the main body.

12. An absorbent article comprising:
    an elongated main body having a skin-side surface and a garment-side surface and including a liquid absorbent layer intended to absorb liquid applied to the skin-side surface and a backsheet appearing on the garment-side surface; and
    leakage preventing walls disposed at equal distances on each side of a longitudinal centerline of the main body and extending longitudinally of the main body, the leakage preventing walls being fixed at longitudinally opposing front and rear ends to the main body and subjected to a longitudinal elastic contractive force between the front and rear ends so as to rise between the front and rear ends with longitudinally extending tops moved away from the skin-side surface;
    wherein each leakage preventing wall is provided, between the front and rear ends, with a constraint portion in which the leakage preventing wall is capable to rise to an allowable rising height from the skin-side surface,
    the allowable rising height within the constraint portion being constrained to be smaller than the allowable rising heights in portions forward and rearward of the constraint portion;

wherein each leakage preventing wall comprises a rising base extending longitudinally along an entire length of the leakage preventing wall along the skin side surface of the main body;

wherein each leakage preventing wall comprises a first inclined panel extending obliquely upward from the rising base, a second inclined panel extending obliquely upward from the first inclined panel in an opposing direction to the first inclined panel, and a skin-contacting panel extending obliquely upward from the second inclined panel in an opposing direction to the second inclined panel;

wherein said skin-contacting panel comprises a fold line, said fold line forming a top of the leakage preventing wall;

wherein the allowable rising height is a distance between the rising base of the leakage preventing wall and the fold line of the skin contacting panel when the leakage preventing wall is forcibly developed;

wherein in the constraint portion, one of the inclined panels is at least partially joined to an adjacent panel comprising the leakage preventing wall, thereby constraining the allowable rising height within the constraint portion; and wherein the constraint portion is located at a midpoint between the front and rear ends of the leakage preventing wall or rearward of the midpoint.

13. An absorbent article according to claim 12, wherein in the constraint portion, the leakage preventing wall is joined to itself so as to constrain the allowable rising height within the constraint portion.

14. An absorbent article according to claim 12, wherein in the constraint portion, the leakage preventing wall is additionally joined to the skin-side surface of the main body.

15. An absorbent article according to claim 12, further comprising:
fold-back flaps projecting outwardly from transversely opposite sides of the main body and configured to be folded back against an outer surface of an undergarment at a crotch part thereof.

16. An absorbent article according to claim 15, further comprising:
rear flaps located rearward of the fold-back flaps, projecting outwardly from the transversely opposite sides of the main body and configured to be placed on an inner surface of the undergarment in an unfolded state, providing the article with a narrow portion that is located between the fold-back flaps and the rear flaps and has a smaller width than a portion including the fold-back flaps.

17. An absorbent article according to claim 16,
wherein the liquid absorbent layer is recessed together with the topsheet to have a pair of longitudinal compressed grooves, a pair of first outside compressed grooves, and a pair of second outside compressed grooves on the skin-side surface of the main body, the longitudinal compressed grooves defining a main absorbent region therebetween, the first outside compressed grooves being disposed on both sides of the main absorbent region at a forward side from a line connecting the constraint portions, and the second outside compressed grooves being disposed on both sides of the main absorbent region at a rear side from the line connecting the constraint portions, and
wherein first and second outside compressed grooves on each side of the main absorbent region are discontinuous with respect to one another in the narrow portion.

18. An absorbent article according to claim 12, wherein each leakage preventing wall has a free end disposed laterally outward, extending perpendicularly away from the longitudinal centerline of the main body.

* * * * *